(12) United States Patent
Bagwandeen

(10) Patent No.: US 8,954,554 B2
(45) Date of Patent: Feb. 10, 2015

(54) SYSTEMS AND METHODS FOR TRANSFERRING REMOTE CONTEXT

(75) Inventor: Hanif George Bagwandeen, Boston, MA (US)

(73) Assignee: General Electric Company, Schenectady, NY (US)

( * ) Notice: Subject to any disclaimer, the term of this patent is extended or adjusted under 35 U.S.C. 154(b) by 770 days.

(21) Appl. No.: 12/833,456

(22) Filed: Jul. 9, 2010

(65) Prior Publication Data
US 2012/0011237 A1 Jan. 12, 2012

(51) Int. Cl.
*G06F 15/173* (2006.01)
*G06F 19/00* (2011.01)

(52) U.S. Cl.
CPC .................. *G06F 19/3406* (2013.01)
USPC ............ 709/223; 709/226; 709/227; 370/338

(58) Field of Classification Search
USPC .................. 709/223, 227; 370/338
See application file for complete search history.

(56) References Cited

U.S. PATENT DOCUMENTS

| | | | |
|---|---|---|---|
| 5,784,562 A * | 7/1998 | Diener ........................ | 709/217 |
| 5,920,479 A * | 7/1999 | Sojoodi et al. ................ | 700/86 |
| 6,993,556 B1 | 1/2006 | Seliger et al. | |
| 7,334,031 B2 | 2/2008 | Royer et al. | |
| 7,565,422 B2 * | 7/2009 | Campbell et al. ............. | 709/223 |
| 8,051,179 B2 * | 11/2011 | Angal et al. ................... | 709/227 |
| 2002/0138624 A1 * | 9/2002 | Esenther ........................ | 709/227 |
| 2002/0147938 A1 * | 10/2002 | Hamilton et al. ................. | 714/6 |
| 2003/0041147 A1 * | 2/2003 | van den Oord et al. ........ | 709/227 |
| 2003/0084165 A1 * | 5/2003 | Kjellberg et al. ............. | 709/227 |
| 2004/0205177 A1 * | 10/2004 | Levy et al. .................... | 709/223 |
| 2005/0066012 A1 * | 3/2005 | Campbell et al. ............. | 709/217 |
| 2005/0201345 A1 * | 9/2005 | Williamson ................. | 370/338 |
| 2005/0278392 A1 * | 12/2005 | Hansen et al. ................. | 707/201 |
| 2006/0053215 A1 * | 3/2006 | Sharma ......................... | 709/223 |
| 2007/0192326 A1 * | 8/2007 | Angal et al. ..................... | 707/10 |
| 2007/0192487 A1 * | 8/2007 | Jakobson ....................... | 709/225 |
| 2009/0138606 A1 * | 5/2009 | Moran et al. .................. | 709/227 |
| 2010/0268940 A1 * | 10/2010 | Pahlavan et al. .............. | 713/155 |
| 2010/0268941 A1 * | 10/2010 | Pahlavan et al. .............. | 713/155 |
| 2011/0131335 A1 * | 6/2011 | Spaltro et al. ................. | 709/228 |
| 2011/0225230 A1 * | 9/2011 | Russ ............................. | 709/203 |
| 2011/0296043 A1 * | 12/2011 | Sutton et al. .................. | 709/229 |
| 2012/0115483 A1 * | 5/2012 | Noldus et al. ................. | 455/436 |

\* cited by examiner

*Primary Examiner* — Razu Miah
(74) *Attorney, Agent, or Firm* — Hanley, Flight and Zimmerman, LLC

(57) ABSTRACT

Example systems and methods provide remote context transfer and session termination. A computer-implemented method for remote context transfer between user sessions with a clinical information system includes accepting a user log on request for a user session at a first clinical information system; identifying one or more open sessions associated with the user; saving a context associated with one of the one or more open sessions; terminating the one or more open sessions identified as associated with the user; and transferring the saved context to the user session at the first clinical information system for use by the user in the user session.

16 Claims, 6 Drawing Sheets

SELECT LOGGED-IN USERS

USERNAME:
FULLNAME:
IP ADDRESS:
ROLE: [ALL ENTRIES] ▼
SYSTEM: [ALL ENTRIES] ▼
SESSION STATE: [ALL ENTRIES] ▼
DEVICE:
DEVICE LOCATION:

[SEARCH] [CLEAR] [CANCEL]

[TERMINATE] [REFRESH]

| USERNAME | FULL NAME | USER ACTIVE | DEACTIVATE USER | EMAIL | IP ADDRESS | SESSION START TIME | SYSTEM |
|---|---|---|---|---|---|---|---|
| ☐ ADMIN | ADMINISTRATOR | YES | ☐ | | 3.230.17.110 | 2008-10-28 12:51:09 | IDXWFADMDOTNET |
| ☐ ADMIN | ADMINISTRATOR | YES | ☐ | | 3.230.17.110 | 2008-10-28 12:51:13 | IDXWFADMDOTNET |
| ☐ ADMIN | ADMINISTRATOR | YES | ☐ | | 3.230.17.110 | 2008-10-29 12:30:42 | IDXWFADMDOTNET |
| ☐ HANIF | HANIF | YES | ☐ | | 3.230.17.110 | 2008-10-29 12:30:51 | IDXWFADMDOTNET |
| ☐ HS | HOMER SIMPSON | YES | ☐ | | 3.230.17.110 | 2008-10-29 12:30:30 | IDXWFADMDOTNET |
| ☐ TESTER | TESTER | YES | ☐ | | 3.230.17.110 | 2008-10-29 12:30:20 | CFTESTHARNESS |

SYSTEMS AND METHODS FOR TRANSFERRING REMOTE CONTEXT

BACKGROUND

Clinical information has become an important part of the diagnosis and treatment of a patient. In many cases, clinical information is stored and accessible in a variety of systems in a variety of locations. Currently, user login at several separate systems introduces delay and repetition that can impact performance and negatively influence the diagnosis and treatment of patients.

BRIEF SUMMARY

Certain embodiments of the present invention provide systems and methods for context transfer.

Certain examples provide a computer-implemented method for remote context transfer between user sessions with a clinical information system. The method includes accepting a user log on request for a user session at a first clinical information system; identifying one or more open sessions associated with the user; saving a context associated with one of the one or more open sessions; terminating the one or more open sessions identified as associated with the user; and transferring the saved context to the user session at the first clinical information system for use by the user in the user session.

Certain examples provide a non-transitory computer-readable storage medium having a set of instructions stored thereon which, when executed, instruct a processor to implement a method for remote context transfer between user sessions with a clinical information system. The method includes accepting a user log on request for a user session at a first clinical information system; identifying one or more open sessions associated with the user; saving a context associated with one of the one or more open sessions; terminating the one or more open sessions identified as associated with the user; and transferring the saved context to the user session at the first clinical information system for use by the user in the user session.

Certain examples provide a clinical context and session management system including a processor connected to a memory. The processor is programmed to facilitate clinical context and session management by implementing a monitor. The monitor is to identify one or more open sessions associated with a user at initiation of a user login request for a user session. The monitor is to trigger a clinical information system to save at least one of a patient context and a user context associated with one of the one or more open sessions and terminate the one or more open sessions identified as associated with the user. The monitor is to facilitate transfer of the saved at least one of a patient context and a user context to the user session for use by the user in the user session.

BRIEF DESCRIPTION OF SEVERAL VIEWS OF THE DRAWINGS

FIG. 3 shows an example session management dashboard.

Figure 1:
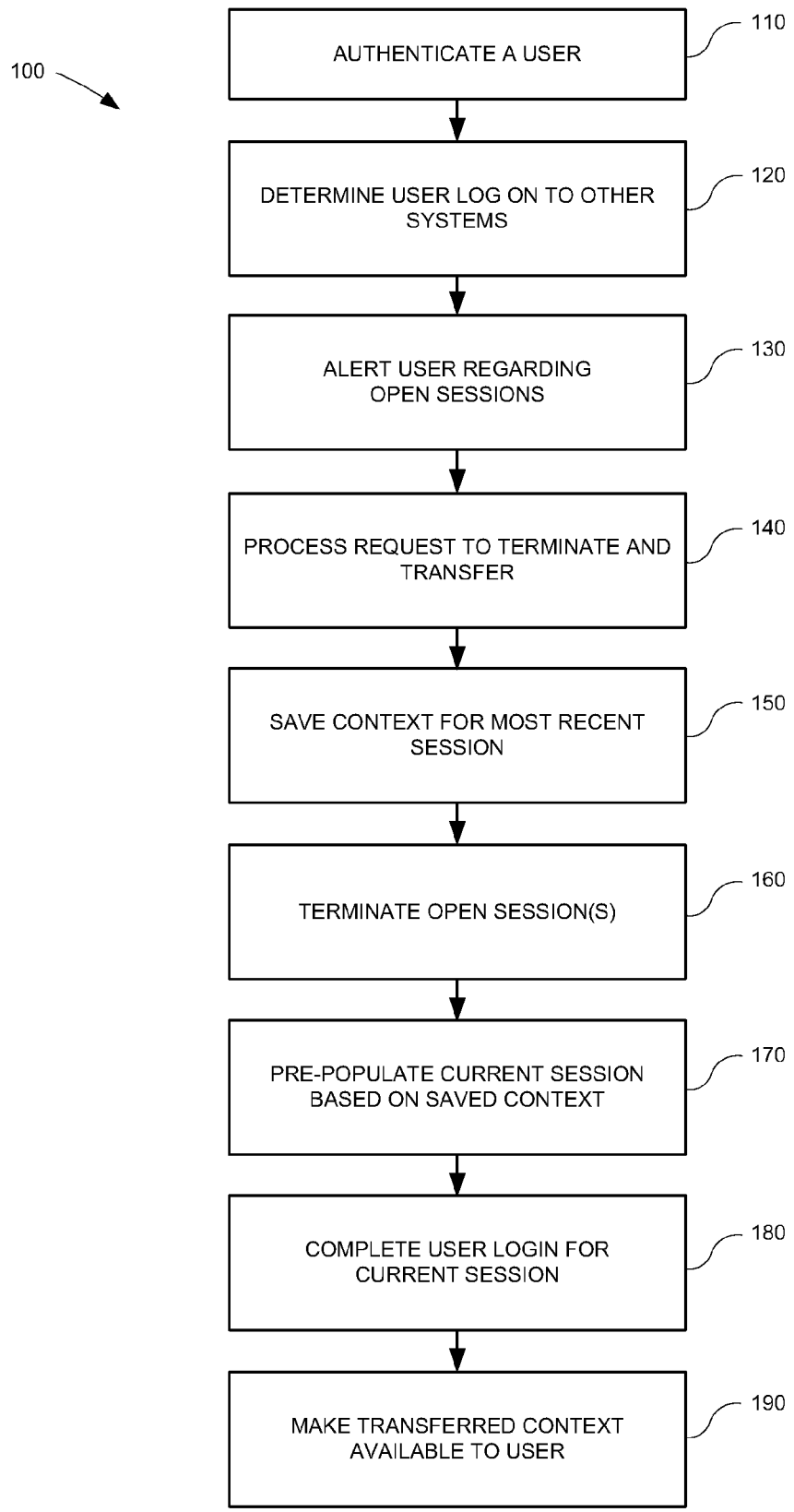
FIG. 1 illustrates a flow diagram for an example method for user and clinical information system interaction for remote context transfer.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Certain examples provide systems and methods for remote user session identification, termination, and context transfer. Certain examples allow a user to save a user/patient context from another open session and resume that context in a local session on a different machine. Certain examples facilitate context saving and restoration to improve user workflow.

Although the following discloses example methods, systems, articles of manufacture, and apparatus including, among other components, software executed on hardware, it should be noted that such methods and apparatus are merely illustrative and should not be considered as limiting. For example, it is contemplated that any or all of these hardware and software components could be embodied exclusively in hardware, exclusively in software, exclusively in firmware, or in any combination of hardware, software, and/or firmware. Accordingly, while the following describes example methods, systems, articles of manufacture, and apparatus, the examples provided are not the only way to implement such methods, systems, articles of manufacture, and apparatus.

When any of the appended claims are read to cover a purely software and/or firmware implementation, at least one of the elements in an at least one example is hereby expressly defined to include a tangible medium such as a memory, DVD, Blu-ray, CD, flash, USB drive, etc. storing the software and/or firmware.

A web framework, such as GE's Centricity Framework™, is a framework for providing web-based healthcare applications and associated information. Using the framework, a patient and/or provider context can be shared. For example, a GE Centricity Business™ user locates a patient in a scheduling module and can then "click on" or otherwise select a link to open the patient's chart in a Centricity EMR™ application. The Electronic Medical Record (EMR) runs in the web framework as well.

Context management is a dynamic computer process that uses "subjects" or targets of data in one application to point to data resident in a separate application also containing the same subject, for example. Context Management allows users to choose a subject once in one application and have all other applications including information regarding that same subject 'tune' to the data they include, thus obviating the need to redundantly select the same subject in the varying applications.

For example, in the healthcare industry, multiple applications operating "in context" using a context manager allow a user to select a patient (e.g., the subject) in one application, and, when the user enters another application, that patient's information is already pre-fetched and presented, obviating the need to re-select the patient in the second application. That is, context management enables clinicians to select a patient's name once in an application and have their screens automatically populate with links to that patient in other applications.

A clinical context includes a set of clinical context subjects. Each subject represents a real-world entity, such as a particular patient, or concept, such as a specific encounter with a patient. By sharing context, applications are able to work together to follow a user's thoughts and actions as the user interacts with a set of applications. These applications are said to be "clinically linked".

Context management can be used in Patient Information Aggregation Platforms (PIAP) such as Portals, for example. Context Management can be used in both HL7 Clinical Context Object Workgroup standard committee (CCOW) and non-CCOW compliant applications. CCOW has created a standardized protocol enabling applications to function in a "context aware" state. The CCOW standard helps facilitate a more robust, and near "plug-and-play" interoperability across disparate applications. Additionally, the Health Level Seven (HL7) Context Management Standard (CMS) defines a standard for automatic coordination and synchronization of disparate healthcare applications that reside on the same clinical desktop.

The CMS defines a Context Management Architecture (CMA), which provides a format for independent applications to share data that describe a common clinical context. Under the CMA, responsibility for managing the common context is centralized in a common facility that is responsible for coordinating the sharing of the context among the applications. In some examples, a set of name-value pairs represent key summary information about the common context (e.g., patient name and medical record number).

The CMA maintains a single authentic copy of the common context for each common context system. Applications can choose to cache context data and/or can access the authentic copy when needed. Applications can also selectively read or write specific context data name-value pairs. When the context changes, an application is only informed about the change and is not provided with the data that has changed. The application can selectively access the change data.

HL7 CMA subjects and associated context data items include core subjects such as patient, encounter, observation, user, and certificate, and their respective context data items. Organizations, such as healthcare provider institutions and vendors, can define their own context subjects and data items. These items are in addition to the standard subjects and the standard items defined for the standard subjects.

GE's Centricity Framework™ offers developers a way to integrate separate GE products, while consolidating sign-on and security to a single point of entry. The Centricity Framework™ provides a consistent presentation of login, navigation (e.g., menus), and patient banner. Hosted products share context information and can offer cross-product workflows, regardless of their user interface (UI) technology.

Centricity Framework 5.0 (CF 5.0) offers a choice of two client desktop solutions (both involving Microsoft .NET™ 2.0 on the client desktop). A first client desktop solution includes a traditional browser-based Web client. A second client desktop solution includes Iris, a Microsoft .NET-based client solution that does not require Internet Explorer (e.g., based on Microsoft smart client technology). The Centricity Framework 5.0 supports a single sign-on (SSO) solution and a context manager, for example.

Communications between the CF and a Web Framework (WF) server can be facilitated via XML-based service calls. Each instance of the CF exposes a certain URL (Uniform Resource Locator) as a handler for all service calls. This URL can be found in the DataURL tag in the Serverinfo.xml file which is located in the WF's main web folder, for example. CF enables the use of a security plug-in to implement an alternate authentication mechanism in place of the standard Framework username/password check. If a security plug-in is used, the plug-in performs server-side authentication of users or of authentication tokens generated on the client. The Framework provides plug-ins for Kerberos (v4.01), RSA SecurID (v5.0), CCOW userlink (v4.0), CCOW/LDAP integration (v4.03), etc.

In some examples, a system enables Web applications to be integrated into process involving concurrent operation of applications. The system specifies the rules for conveying URL data and other data between applications. The system employs a managing application and services (e.g., a session manager) to facilitate application session management. The system employs by a first (parent) application for supporting concurrent operation with other (children) applications. The system involves an entitlement processor for authorizing user access to the first (parent) application in response to validation of user identification information. The system involves a communication processor for communicating a session initiation request to a managing application to initiate generation of a session identifier particular to a user initiated session.

The session manager is used by the managed applications to reference global data that is essential to a workflow. Such global data includes user identification information, a shared key used for the encryption of URL data, and a common URL to be used for handling logoff and logon function, for example. The session manager is regularly notified of activities from the applications to prevent an inactivity timeout while a user is active in another concurrent application. The session manager employs a system protocol for passing session context information between applications via URL query or form data.

Session context information includes a session identifier (used by the managed applications to identify a user initiated session in communicating with manager), a hash value (used by the managed applications to validate that a received URL has not been corrupted), and application specific data (can be encrypted), for example. The session manager uses a unique session identifier (SID) for each new session (e.g., to protect against corruption and replay of a URL). In addition, to avoid redirection, the parent application can generate a URL link with an embedded hash value from the domain, port and file path name of the URL (e.g. using RSA MD5). Communication can occur via HTTP, TCP/IP, and/or other similar communication protocol to facilitate exchange of data between a client browser and application(s), between application(s) and the session manager, etc.

Certain examples allow a user to remotely shut down another application and take the patient and/or provider context from that application to transfer it to the new application. Remote context transfer and application shutdown provides security within context sharing, for example.

In an example Microsoft .NET™ implementation, a port is opened to allow new applications to connect to the port and issue logout requests for another executing application. For example, first, an application begins execution and opens a communication port. The application starts a listener with the .NET framework, which "listens" or monitors to detect other applications. Any further applications that are opened can send a request to the first application to log out the user of the first application. When that user is logged out, a context of a patient that the user was reviewing and/or a user context itself is saved to a database.

When the user starts a second application, the user receives a message asking whether he or she wishes to shut down the first application and retrieve its patient and/or user context. The first application receives a message indicating the pending shutdown or log out. The context (e.g., patient and/or user) is saved at application shutdown, and then the second application is allowed to take the saved context from the database and open up the patient and/or user context in its session.

To retrieve a saved patient and/or user context, a database and/or other data storage is queried to identify and retrieve the stored context. Credentials (e.g., username, password, card-based identifier, biometric identifier, etc.) can be requested to allow access to and execution of the first and/or second application. Credentials are used to identify and retrieve context for the second application. Credentials can be used to save and then retrieve context information, for example.

A context can include information such as a patient identifier, a list of previously viewed patients, a recently found list of patients (e.g., formulated as a drop-down menu for user selection), an active document being viewed at the time of context saving, a list of previously viewed documents (e.g., formulated as a drop-down menu for user selection), an active screen (e.g., not just a document per se but also, for example, a user summary screen), etc. In some examples, a context can allow a user to resume activity at a place in an application at which the user can previously stopped his or her work. In some examples, a context transfer allows a user to be brought back to a particular application. Applications can relate to any clinical information system, such as a picture archiving and communication system (PACS), a radiology information system (RIS), an electronic medical records (EMR) system, a personal health record (PHR) system, a laboratory information system (LIS), a cardiovascular information system (CVIS), a hospital information system (HIS), an imaging modality-related system, and/or other clinical information system (CIS).

In certain examples, in order to facilitate smooth on-the-fly context transfers, delay in context saving, log in and log out can be accommodated. If a delay occurs in the first application when a call to logout is issued, the patient and/or user context is saved before the second application can log in. A built in wait time can be added to allow certain phases to complete, including a check to see if the first application session has been logged out before moving forward with the second application.

Using automatic, remote context transfer can help save a user's time in having to open a new application and manually reload the context. Upon load of a new application session, initiation of the session can include a check to see if a saved context exists to be loaded.

In certain examples, the same user can be logged into one or more instances of a Clinical Information System at the same time. Users of a single Clinical Information System can move between systems (e.g., instances) and maintain contextual data, even if they have not logged out of previous system.

The definition of context can be configurable per Clinical Information System. For example, context information can include: the Patient ID being accessed, the list of previously viewed Patient IDs, the active document being view, the list of previously viewed documents, the active screen, etc.

In operation, for example, a user has logged into a system on device A, accesses patient information, and leaves herself logged into device A. She then goes to device B and wants to pick up where she left off, e.g., viewing the same patient information as on device A. She wants context information transferred from her session on device A to her session on device B.

Upon authentication into a Clinical Information System, the system 1) detects that the user has an established session (e.g., the user already logged into another system) or sessions opened and 2) allows context information associated with the "most recent" session to be transferred to the local session (e.g., transferred to the system for which the user is currently being logged in).

In certain examples, a Clinical Information System can receive requests from other systems in order to allow a remote logout of a user. When the system detects this request for a remote logout, the system saves user and/or patient context. The system can also detect that a user is logged into other system(s) and send remote logout requests to those system(s) as needed.

FIG. 1 illustrates a flow diagram for an example method 100 for user and clinical information system interaction for remote context transfer. FIG. 1 depicts an example flow diagram representative of processes that may be implemented using, for example, computer readable instructions that may be used to facilitate remote user logout and context transfer. The example processes of FIG. 1 may be performed using a processor, a controller and/or any other suitable processing device. For example, the example processes of FIG. 1 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 1 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 1 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 1 may be implemented manually or as any combination(s) of any of the foregoing techniques, for example, any combination of firmware, software, discrete logic and/or hardware. Further, although the example processes of FIG. 1 are described with reference to the flow diagram of FIG. 1, other methods of implementing the processes of FIG. 1 may be employed. For example, the order of execution of the blocks may be changed, and/or some of the blocks described may be changed, eliminated, sub-divided, or combined. Additionally, any or all of the example processes of FIG. 1 may be performed sequentially and/or in parallel by, for example, separate processing threads, processors, devices, discrete logic, circuits, etc.

Referring to FIG. 1, at 110, user is authenticated with respect to a Clinical Information System. At 120, after a user has been successfully authenticated, user log in to other system(s) is determined by the clinical information system.

At 130, the user is alerted to the multiple open sessions. For example, the system displays the message, "You have <# of open sessions> other sessions open. Do you want to terminate all other sessions and transfer context from the most recent session?" At 140, user confirmation of termination and context (e.g., patient and/or user) transfer is processed.

At 150, user and/or patient context is saved for the most recent user session (e.g., the open session with the most recent start date and time). At 160, the user's sessions are terminated (e.g., logged out). At 170, saved context information is used to pre-populate data on applicable screens and/or store data in memory. At 180, the user login process is completed for the new session. At 190, the context from a previous session is made available to the user who can continue with his/her work.

As described herein, the method 100 can be implemented using the mobile device in one or more combinations of hardware, software, and/or firmware, for example. The method 100 can operate with the mobile device in conjunction with one or more external systems (e.g., data sources, healthcare information systems (RIS, PACS, CVIS, HIS, EMR, EHR, PHR, etc.), archives, imaging modalities, etc.). One or more components of the method 100 can be reordered, eliminated, and/or repeated based on a particular implementation, for example.

Thus, certain examples help enable more efficient workflows in Clinical Information Systems by allowing a user to transfer context from the most recent remote session to the local session. Certain examples help reduce security risks caused by unwanted, opened sessions to a Clinical Information System by allowing a user to terminate his/her own remote sessions.

Certain examples provide a technical effect of enabling remote termination of opened sessions from any instance of a Clinical Information System while saving context information based on this remote termination. Certain examples provide reloading a user's context (e.g., patient and/or user context) at his/her discretion.

Figure 2:
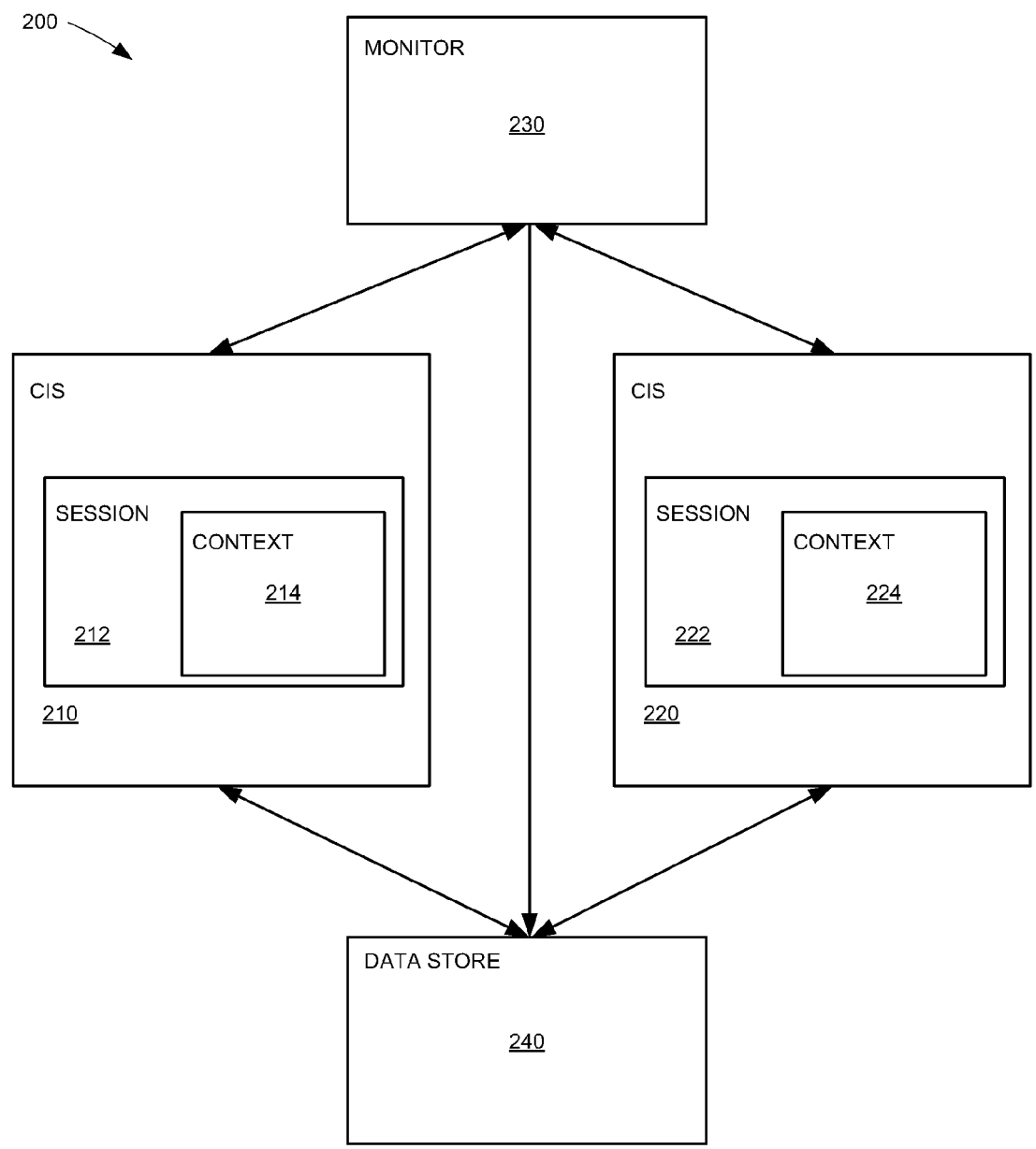
FIG. 2 illustrates an example system enabling remote transfer of context and session termination with respect to one or more clinical information systems.

FIG. 2 illustrates an example system 200 enabling remote transfer of context and session termination with respect to one or more clinical information systems. The system 200 includes a first clinical information system (CIS) 210 and a second CIS 220. The first CIS 210 includes a first user session 212 and a first context 214 within the session 212. The context 214 can be a user and/or patient context, for example. The second CIS 220 includes a second user session 222 and a second context 224 within the session 222. The context 224 can be a user and/or patient context, for example. A monitor 230 monitors applications executing on the first CIS 210 and second CIS 220 to identify additional instances of a user session.

When the monitor 230 detects that the first user session 212 on the first CIS 210 remains open when the second user session 222 is initiated, the monitor 230 communicates with the first CIS 210 to indicate closure of the first user session 212 and saving of the first context 214 to a data store 240. The user can be prompted to save and/or logout, and/or the monitor 230 can facilitate an automated save and/or logout of the first context 214 and user session 212. Once the first context 214 has been saved and the first user session 212 has been terminated, the second user session 222 identifies and retrieves the saved first context 214 from the data store 240 and provides it to the user as the second context 224.

Using the monitor 230, a user at the second CIS 220 and/or an administration can view logged-in user session(s) 212 and associated device(s) 210. A user can terminate his/her own remote session 212. An administrator can also terminate a user's remote session 212. The user can terminate his/her own remote session 212 and transfer his/her user and/or patient context 214 from that remote session 212 to the local session 222.

As depicted, for example, in FIG. 3, an administrator can be authorized to view and access device, session, and context information via a session management dashboard 300, for example. A dashboard results grid can include information such as Username, Full Name, User Active, Deactivate User, Email, IP Address, Role, Session Start Time, System ID, Session State, Device ID, Device Location, Device Description, Device Active, and Deactivate Device. In certain examples, an administration can search using criteria such as Username, Full Name, IP Address, Device ID, Device Location, System ID, Role, and Session State. From the dashboard an administrator, authorized to access this functionality, can terminate one or more associated users. When the Administrator terminates remote sessions for a given user/device, the remote session context with the latest session start time is saved. In certain examples, an administrator can set a preference to provide a user with the option of terminating his/her remote session. In certain examples, a user is allowed to log in, even if the user decides not to terminate his/her remote session.

When a user is prompted to terminate his/her remote session, the user is prompted to transfer context information (e.g., patient and/or user context) from the remote session to the local session. In certain examples, a session logout can be configured to allow an automatic and/or user-selected grace period, such as one, five, or fifteen minutes, before session termination. In certain examples, if a grace period is used, the time remaining until termination is displayed in the remote user's toolbar or status bar. A user can receive one or more default and/or custom messages regarding termination and/or context transfer.

Upon log in, a user with a single session open (not including the current session) can be prompted with a message box or other dialog indicating "You have one other session open. Do you want to terminate that session?" The user can respond by selecting yes or no. Additionally, the user can be asked if he/she would like to save and/or transfer the context in which he/she was working for the remote open session. A user with multiple open sessions can be prompted to terminate one or more of the open sessions and to transfer context from one of the sessions being terminated to the current user session.

In certain examples, all sessions other than the session initiating a log out request are considered remote sessions. Thus, in those examples, event client sessions on the same/machine device other than the requesting session. In certain examples, a username can be selected to log out all remote sessions for that username, regardless of other identifier, such as system ID.

In certain examples, a context save is facilitated using a client side socket listener to handle logout requests sent via a framework server. In examples having multiple active remote sessions, one or more criteria, such as most recent start time, dictates which context is transferred from a remote session to the local session. In certain examples, a loop or delay can be executed after a context save and/or logout is initiated to make sure that the action is completed before advancing to a next portion of the process.

Certain examples support Clinical Context Object Workgroup (CCOW) context management. In some CCOW logout processing (assuming CCOW is enabled and user context is set) a logout terminates all joined sessions. Since a user may be requesting his/her sessions (on that computer/device) be logged-out, CCOW logout behavior would interfere with this process. Therefore, a CCOW logout can be skipped if the user has a settings, such as a SessionTerminateRemotely preference, set to "Terminate" or "TerminateAndTransferContext", and decides to logout out all his/her open sessions.

Figure 4:
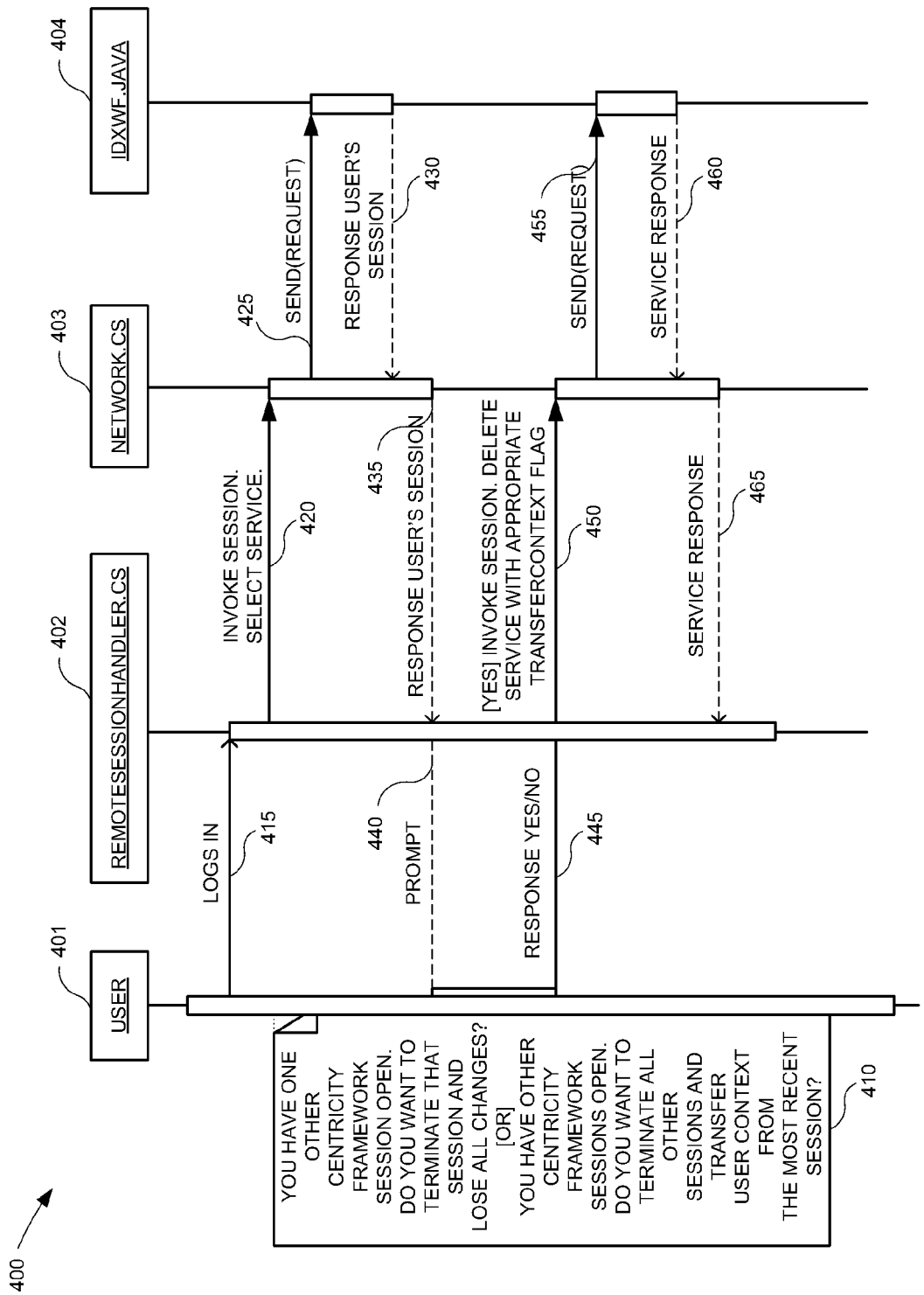
FIG. 4 depicts an example sequence diagram for a process facilitating remote user session log out.

FIG. 4 depicts an example sequence diagram for a process 400 facilitating remote user session log out. FIG. 4 depicts an example flow diagram representative of processes that may be implemented using, for example, computer readable instructions that may be used to facilitate remote user logout and context transfer. The example processes of FIG. 4 may be performed using a processor, a controller and/or any other suitable processing device. For example, the example processes of FIG. 4 may be implemented using coded instructions (e.g., computer readable instructions) stored on a tangible computer readable medium such as a flash memory, a read-only memory (ROM), and/or a random-access memory (RAM). As used herein, the term tangible computer readable medium is expressly defined to include any type of computer readable storage and to exclude propagating signals. Additionally or alternatively, the example processes of FIG. 4 may be implemented using coded instructions (e.g., computer readable instructions) stored on a non-transitory computer readable medium such as a flash memory, a read-only memory (ROM), a random-access memory (RAM), a cache, or any other storage media in which information is stored for any duration (e.g., for extended time periods, permanently, brief instances, for temporarily buffering, and/or for caching of the information). As used herein, the term non-transitory computer readable medium is expressly defined to include any type of computer readable medium and to exclude propagating signals.

Alternatively, some or all of the example processes of FIG. 4 may be implemented using any combination(s) of application specific integrated circuit(s) (ASIC(s)), programmable logic device(s) (PLD(s)), field programmable logic device(s) (FPLD(s)), discrete logic, hardware, firmware, etc. Also, some or all of the example processes of FIG. 4 may be implemented manually or as any combination(s) of any of the foregoing techniques, for example, any combination of firmware, software, discrete logic and/or hardware. Further, although the example processes of FIG. 4 are described with reference to the flow diagram of FIG. 4, other methods of implementing the processes of FIG. 4 may be employed. For example, the order of execution of the blocks may be changed, and/or some of the blocks described may be changed, eliminated, sub-divided, or combined. Additionally, any or all of the example processes of FIG. 4 may be performed sequentially and/or in parallel by, for example, separate processing threads, processors, devices, discrete logic, circuits, etc.

Turning to FIG. 4, at 410, a user 401 initiates a log in to a session. At 415, a remote session handler 402 invokes a session selection service. At 420, a network module 403 sends a request to a java service application 404 to identify open user session(s). For example, the application 404 matches the user's username to open sessions to identify those session(s) associated with the same user.

At 425, a response identifying the user's session(s) is sent back to the network drier 403. At 430, the response is relayed to the remote session handler 402. At 435, the remote session handler 402 prompts the user 401 regarding the open session (s). For example, at 440, the user receives a message at a new session login indicating that other session(s) remain open within the software framework. The user is asked whether he or she wishes to close the other open session(s) and transfer a user and/or patient context to the current session or lose the open context information.

At 445, a user 401 response (e.g., yes, no, or particular item (e.g., session) selection) is provided to the remote session handler 402. At 450, if the response is "yes", then a session delete service is invoked with an appropriate context transfer flag based on user response (e.g., to transfer or not to transfer context).

At 455, the network 403 sends the session delete server request to the java service application 404. At 460, the application 404 generates a session delete service response. At 465, the service response is relayed by the network 403 to the remote session handler 402.

Figure 5:
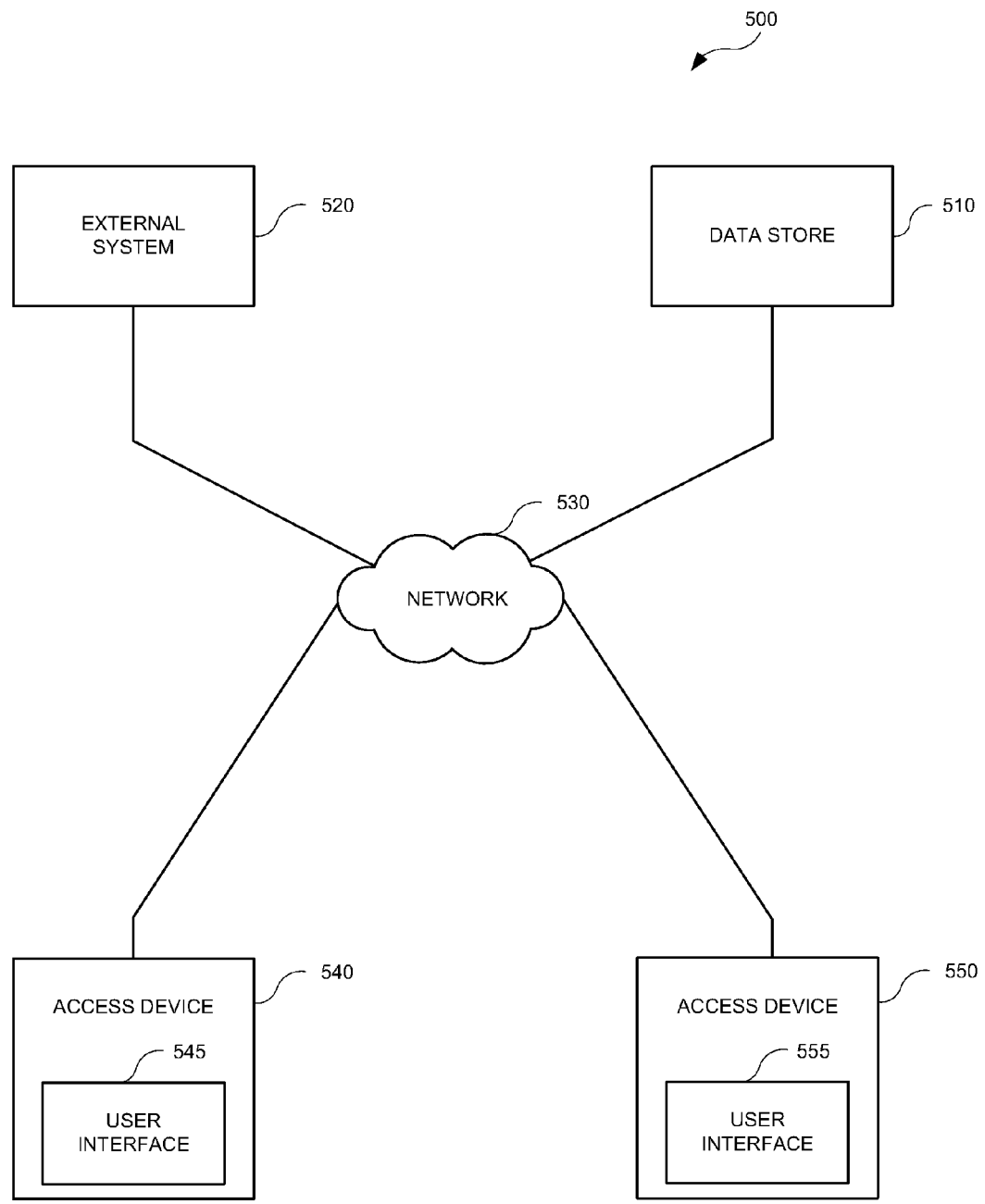
FIG. 5 shows an example clinical enterprise system.

Systems and methods described above can be included in a clinical enterprise system, such as example clinical enterprise system 500 depicted in FIG. 5. The system 500 includes a data source 510, an external system 520, a network 530, a first access device 540 with a first user interface 545, and a second access device 550 with a second user interface 555. In some examples, the data source 510 and the external system 520 can be implemented in a single system. In some examples multiple data sources 510 and/or external systems 520 can be in communication via the network 530. The data source 510 and the external system 520 can communicate with one or more of the access devices 540, 550 via the network 530. One or more of the access devices 540, 550 can communicate with the data source 510 and/or the external system 520 via the network 530. In some examples, the access devices 540, 550 can communicate with one another via the network 530 using a communication interface (e.g., a wired or wireless communications connector/connection (e.g., a card, board, cable, wire, and/or other adapter, such as Ethernet, IEEE 1394, USB, serial port, parallel port, etc.). The network 530 can be implemented by, for example, the Internet, an intranet, a private network, a wired or wireless Local Area Network, a wired or wireless Wide Area Network, a cellular network, and/or any other suitable network.

The data source 510 and/or the external system 520 can provide patient records, images, reports, scheduling, guidelines, best practices and/or other data/applications to the access devices 540, 550. In some examples, the data source 510 can receive information associated with a session or conference and/or other information from the access devices 540, 550. In some examples, the external system 520 can receive information associated with a session or conference and/or other information from the access devices 540, 550. The data source 510 and/or the external system 520 can be implemented using a system such as a PACS, RIS, HIS, CVIS, EMR, archive, data warehouse, imaging modality (e.g., x-ray, CT, MR, ultrasound, nuclear imaging, etc.), payer system, provider scheduling system, guideline source, hospital cost data system, and/or other healthcare system.

The access devices 540, 550 can be implemented using a workstation (a laptop, a desktop, a tablet computer, etc.) or a mobile device, for example. Some mobile devices include smart phones (e.g., BlackBerry™, iPhone™, etc.), Mobile Internet Devices (MID), personal digital assistants, cellular phones, handheld computers, tablet computers (iPad™), etc., for example. In some examples, security standards, virtual private network access, encryption, etc., can be used to maintain a secure connection between the access devices 540, 550, data source 510, and/or external system 520 via the network 530. In some examples, one or more of the access devices 540, 550 can be integrated with the data source 510 and/or external system 520, and the network 530 can include wires, cables and/or other connection(s) internally and/or logically connecting the system components.

In some examples, the access device 540, 550 can be implemented using a smart phone (e.g., BlackBerry™, iPhone™, iPad™, etc.), Mobile Internet device (MID), personal digital assistant, cellular phone, handheld computer, etc. The access device 540, 550 includes a processor retrieving data, executing functionality, and storing data at the access device 540, 550, data source 510, and/or external system 530. The processor drives a graphical user interface (GUI) 545, 555 providing information and functionality to a user and receiving user input to control the device 540, 550, edit information, etc. The GUI 545, 555 can include a touch pad/screen integrated with and/or attached to the access device 540, 550, for example. The device 540, 550 includes one or more internal memories and/or other data stores including data and tools. Data storage can include any of a variety of internal and/or external memory, disk, Bluetooth remote storage communicating with the access device 540, 550, etc. Alternatively or in addition to gesture-based navigation/manipulation, a detector, such as an accelerometer, position encoder (e.g., absolute, incremental, optical, analog, digital, etc.), global positioning sensor, and/or other sensor, etc., can be used to detect motion of the access device 540, 550 (e.g., shaking, rotating or twisting, left/right turn, forward/backward motion, etc.). Detected motion can be used to affect operation and/or outcomes at the access device 540, 550. The access device 540, 550 processor can include and/or communicate with a communication interface component to query, retrieve, and/or transmit data to and/or from a remote device, for example.

The access device 540, 550 can be configured to follow standards and protocols that mandate a description or identifier for the communicating component (including but not limited to a network device MAC address, a phone number, a GSM phone serial number, an International Mobile Equipment Identifier, and/or other device identifying feature). These identifiers can fulfill a security requirement for device authentication. The identifier is used in combination with a front-end user interface component that leverages an input device such as but not limited to; Personal Identification Number, Keyword, Drawing/Writing a signature (including but not limited to; a textual drawing, drawing a symbol, drawing a pattern, performing a gesture, etc.), etc., to provide a quick, natural, and intuitive method of authentication. Feedback can be provided to the user regarding successful/unsuccessful authentication through display of animation effects on a mobile device user interface. For example, the device can produce a shaking of the screen when user authentication fails. Security standards, virtual private network access, encryption, etc., can be used to maintain a secure connection.

For example, an end user launches a secure application (including but not limited to a clinical application requiring a degree of security). The application reads the unique identifying features of the device and performs an authentication "hand-shake" with the server or data-providing system. This process is automated with no user input or interaction required. After the device has been authenticated, the user is presented with an application/user level authentication screen (including but not limited to a personal identification number (PIN), password/passcode, gesture, etc.) to identify to the application that the user is indeed a valid user. This feature functions as a method to provide device level security as well as an ability to lock the device (e.g., if the user wishes to temporary lock the device but not logout/shutdown the application), for example.

Figure 6:
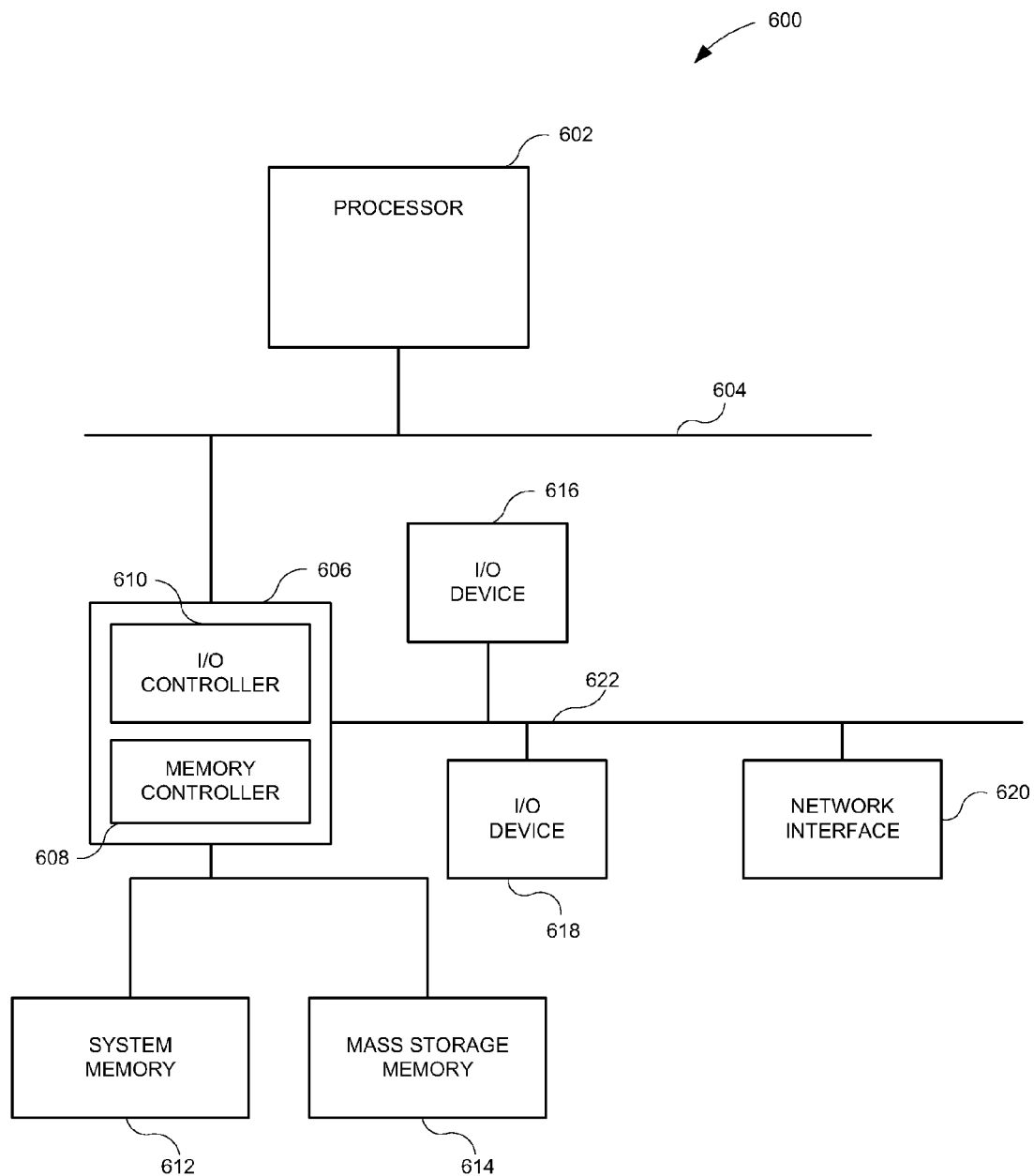
FIG. 6 is a block diagram of an example processor system that may be used to implement the systems, apparatus and methods described herein.

FIG. 6 is a block diagram of an example processor system 610 that may be used to implement the systems, apparatus and methods described herein. As shown in FIG. 6, the processor system 610 includes a processor 612 that is coupled to an interconnection bus 614. The processor 612 may be any suitable processor, processing unit or microprocessor. Although not shown in FIG. 6, the system 610 may be a multi-processor system and, thus, may include one or more additional processors that are identical or similar to the processor 612 and that are communicatively coupled to the interconnection bus 614.

The processor 612 of FIG. 6 is coupled to a chipset 618, which includes a memory controller 620 and an input/output (I/O) controller 622. As is well known, a chipset typically provides I/O and memory management functions as well as a plurality of general purpose and/or special purpose registers, timers, etc. that are accessible or used by one or more processors coupled to the chipset 618. The memory controller 620 performs functions that enable the processor 612 (or processors if there are multiple processors) to access a system memory 624 and a mass storage memory 625.

The system memory 624 may include any desired type of volatile and/or nonvolatile memory such as, for example, static random access memory (SRAM), dynamic random access memory (DRAM), flash memory, read-only memory (ROM), etc. The mass storage memory 625 may include any desired type of mass storage device including hard disk drives, optical drives, tape storage devices, etc.

The I/O controller 622 performs functions that enable the processor 612 to communicate with peripheral input/output (I/O) devices 626 and 628 and a network interface 630 via an I/O bus 632. The I/O devices 626 and 628 may be any desired type of I/O device such as, for example, a keyboard, a video display or monitor, a mouse, etc. The network interface 630 may be, for example, an Ethernet device, an asynchronous transfer mode (ATM) device, an 802.11 device, a DSL modem, a cable modem, a cellular modem, etc. that enables the processor system 610 to communicate with another processor system.

While the memory controller 620 and the I/O controller 622 are depicted in FIG. 6 as separate blocks within the chipset 618, the functions performed by these blocks may be integrated within a single semiconductor circuit or may be implemented using two or more separate integrated circuits.

Thus, certain examples provide an ability to track and control multiple user sessions among one or more clinical systems. Certain examples facilitate context saving and transfer (e.g., a patient context, a user context, etc.) to streamline clinician workflow and improve efficiency in diagnosis, treatment, and patient management. Remote session termination and context transfer provides a technical effect of reducing redundancy and error associated with multiple, disparate sessions and associated context and data. For example, a user can review information at a patient's bedside and pick up at the same place in the same context at a nurse's stations or radiology workstation.

Certain embodiments contemplate methods, systems and computer program products on any machine-readable media to implement functionality described above. Certain embodiments may be implemented using an existing computer processor, or by a special purpose computer processor incorporated for this or another purpose or by a hardwired and/or firmware system, for example.

One or more of the components of the systems and/or steps of the methods described above may be implemented alone or in combination in hardware, firmware, and/or as a set of instructions in software, for example. Certain embodiments may be provided as a set of instructions residing on a computer-readable medium, such as a memory, hard disk, Blu-ray, DVD, or CD, for execution on a general purpose computer or other processing device. Certain embodiments of the present invention may omit one or more of the method steps and/or perform the steps in a different order than the order listed. For example, some steps may not be performed in certain embodiments of the present invention. As a further example, certain steps may be performed in a different temporal order, including simultaneously, than listed above.

Certain embodiments include computer-readable media for carrying or having computer-executable instructions or data structures stored thereon. Such computer-readable media may be any available media that may be accessed by a general purpose or special purpose computer or other machine with a processor. By way of example, such computer-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of computer-executable instructions or data structures and which can be accessed by a general purpose or special purpose computer or other machine with a processor. Combinations of the above are also included within the scope of computer-readable media. Computer-executable instructions comprise, for example, instructions and data which cause a general purpose computer, special purpose computer, or special purpose processing machines to perform a certain function or group of functions.

Generally, computer-executable instructions include routines, programs, objects, components, data structures, etc., that perform particular tasks or implement particular abstract data types. Computer-executable instructions, associated data structures, and program modules represent examples of program code for executing steps of certain methods and systems disclosed herein. The particular sequence of such executable instructions or associated data structures represent examples of corresponding acts for implementing the functions described in such steps.

Embodiments of the present invention may be practiced in a networked environment using logical connections to one or more remote computers having processors. Logical connections may include a local area network (LAN), a wide area network (WAN), a wireless network, a cellular phone network, etc., that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. Embodiments of the invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing the overall system or portions of embodiments of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD ROM or other optical media. The drives and their associated computer-readable media provide nonvolatile storage of computer-executable instructions, data structures, program modules and other data for the computer.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A computer-implemented method for remote context transfer between user sessions with a clinical information system, the method comprising:
   accepting a user log on request for a user session at a first clinical information system;
   identifying one or more open sessions associated with the user;
   saving a clinical context associated with one of the one or more open sessions;
   alerting the user regarding the one or more open sessions and accepting user instruction regarding terminating the one or more open sessions and transferring the context to the user session at the first clinical information system;
   terminating the one or more open sessions identified as associated with the user; and
   transferring the saved context to the user session at the first clinical information system to configure the user session based on the saved context,
   wherein remote termination of the one or more open sessions is enabled from the first clinical information system while saving and making the context available for the user to continue in the context via the user session, wherein transferring the saved context to configure the user session comprises loading the saved context for the user session and pre-populating data from the saved context in one or more user interface screens of the user session,
   and wherein a list of available sessions is displayed via a session management dashboard for one or more users, the session management dashboard to provide device, session, and context information for each available session, the session management dashboard to allow an authorized user to terminate a selected session.

2. The method of claim 1, wherein accepting a user log on request further comprises authenticating the user.

3. The method of claim 1, wherein identifying further comprises identifying one or more open sessions associated with the user at one or more remote clinical information systems.

4. The method of claim 1, wherein identifying further comprises identifying one or more open sessions associated with the user based on a user identifier.

5. The method of claim 4, wherein the identifier comprises a username associated with the user.

6. The method of claim 1, wherein saving a context further comprises saving a context from a most recent of the one or more open sessions.

7. The method of claim 1, wherein the context comprises at least one of a user context and a patient context.

8. A non-transitory computer-readable storage medium having a set of instructions stored thereon which, when executed, instruct a processor to implement a method for remote context transfer between user sessions with a clinical information system, the method comprising:

accepting a user log on request for a user session at a first clinical information system;

identifying one or more open sessions associated with the user;

saving a clinical context associated with one of the one or more open sessions;

alerting the user regarding the one or more open sessions and accepting user instruction regarding terminating the one or more open sessions and transferring the context to the user session at the first clinical information system;

terminating the one or more open sessions identified as associated with the user; and transferring the saved context to the user session at the first clinical information system to configure the user session based on the saved context, wherein remote termination of the one or more open sessions is enabled from the first clinical information system while saving and making the context available for the user to continue in the context via the user session, wherein transferring the saved context to configure the user session comprises loading the saved context for the user session and pre-populating data from the saved context in one or more user interface screens of the user session, and wherein a list of available sessions is displayed via a session management dashboard for one or more users, the session management dashboard to provide device, session, and context information for each available session, the session management dashboard to allow an authorized user to terminate a selected session.

9. The non-transitory computer-readable storage medium of claim 8, wherein identifying further comprises identifying one or more open sessions associated with the user at one or more remote clinical information systems.

10. The non-transitory computer-readable storage medium of claim 8, wherein identifying further comprises identifying one or more open sessions associated with the user based on a user identifier.

11. The non-transitory computer-readable storage medium of claim 8, wherein saving a context further comprises saving a context from a most recent of the one or more open sessions.

12. The non-transitory computer-readable storage medium of claim 8, wherein the context comprises at least one of a user context and a patient context.

13. A clinical context and session management system comprising:

a processor connected to a memory, wherein the processor is programmed to facilitate clinical context and session management by implementing:

a monitor to identify one or more open sessions associated with a user at initiation of a user login request for a user session, the monitor to trigger a clinical information system to save at least one of a patient context and a user context associated with one of the one or more open sessions and terminate the one or more open sessions identified as associated with the user, wherein the monitor is to facilitate transfer of the saved at least one of a patient context and a user context to the user session to configure the user session based on the at least one of the patient context and user context, wherein the monitor is to alert the user regarding the one or more open sessions and accept user instruction regarding terminating the one or more open sessions and transferring the at least one of a patient context and a user context to the user session, wherein remote termination of the one or more open sessions is enabled from the clinical information system while saving and making the at least one of a patient context and a user context available for the user to continue in the context via the user session, and wherein transfer of the saved context to configure the user session comprises loading the saved context for the user session and pre-populating data from the saved context in one or more user interface screens of the user session; and a session management dashboard to display a list of available sessions for one or more users, the session management dashboard to provide device, session, and context information for each available session, the session management dashboard to allow an authorized user to terminate a selected session.

14. The system of claim 13, further comprising an administrative session management dashboard to enable an administrator to monitor users with open sessions and facilitate termination of open sessions and transfer of at least one of a patient context and a user context to a local user session.

15. The system of claim 13, wherein the monitor interacts with a data store in which at least one of a patient context and a user context is saved.

16. The system of claim 13, wherein at least one of a patient context and a user context is saved for transfer from a most recent of the one or more open sessions.

\* \* \* \* \*